United States Patent
Ng et al.

(10) Patent No.: US 9,012,151 B2
(45) Date of Patent: Apr. 21, 2015

(54) METHODS OF DIAGNOSIS AND RISK STRATIFICATION OF ADVERSE EVENTS IN POST MYOCARDIAL INFARCTION PATIENTS USING PRO-ADRENOMEDULLIN

(75) Inventors: Leong Loke Ng, Leicester (GB); Andreas Bergmann, Berlin (DE); Joachim Struck, Berlin (DE); Nils Morgenthaler, Berlin (DE); Jana Papassotiriou, Berlin (DE)

(73) Assignee: B.R.A.H.M.S. GmbH, Hennigsdorf (DE)

( * ) Notice: Subject to any disclaimer, the term of this patent is extended or adjusted under 35 U.S.C. 154(b) by 909 days.

(21) Appl. No.: 11/937,061

(22) Filed: Nov. 8, 2007

(65) Prior Publication Data

US 2008/0213746 A1  Sep. 4, 2008

Related U.S. Application Data

(60) Provisional application No. 60/858,083, filed on Nov. 9, 2006.

(51) Int. Cl.
| | |
|---|---|
| *G01N 33/53* | (2006.01) |
| *A61K 39/00* | (2006.01) |
| *A61K 39/395* | (2006.01) |
| *G01N 33/563* | (2006.01) |
| *A61K 38/00* | (2006.01) |
| *G01N 33/68* | (2006.01) |
| *G01N 33/74* | (2006.01) |

(52) U.S. Cl.
CPC ............ *G01N 33/6893* (2013.01); *G01N 33/74* (2013.01); *G01N 2800/324* (2013.01)

(58) Field of Classification Search
CPC ....... A61K 38/00; A61K 38/04; A61K 38/10; A61K 38/16; G01N 2800/52; G01N 2035/0097; G01N 2800/32; G01N 2333/58; G01N 2800/325; G01N 2800/56; G01N 2800/50; G01N 2800/2871; G01N 2800/54; G01N 2800/324; G01N 33/49; C07K 7/08; C07K 14/58

See application file for complete search history.

(56) References Cited

U.S. PATENT DOCUMENTS

| | | | |
|---|---|---|---|
| 2007/0082363 A1* | 4/2007 | Bougueleret et al. .......... | 435/7.1 |
| 2008/0199966 A1* | 8/2008 | Bergmann et al. .............. | 436/86 |

FOREIGN PATENT DOCUMENTS

| | | | | |
|---|---|---|---|---|
| WO | WO 2004090546 | * | 10/2004 | ............. G01N 33/53 |

OTHER PUBLICATIONS

Hinson et al. 2000. Endocrine Reviews 2:138-167.*
Lim et al 2007. Diabetes Care 30:1513-1519.*
Dieplinger et al 2009. Kidney International 75:408-414.*
Christ-Crain et al (2006. Critical Care 10:1-8.*
Schuetz et al 2007. Endothelium 14:345-351.*
Christ-Crain et al 2005. Critical Care 9:R816-824.*
Vizza et al 2005. Regulatory Peptides 124:187-193.*
de Lemos et al. 2003. Lancet. 362:316-322.*
Masson et al 2008. Am J. Cardiol. 101[suppl]:56A-60A.*
Katyama et a (2004. Internal Medicine 43:1015-1022.*
Katyama et al 2005. Circ J. 69:83-88.*
Richards et al 1998. Circulation 97:1921-1929.*

* cited by examiner

*Primary Examiner* — Shulamith H Shafer
(74) *Attorney, Agent, or Firm* — Novak Druce Connolly Bove + Quigg LLP

(57) ABSTRACT

The invention provides methods for the diagnosis and risk stratification of adverse events in post-myocardial infarction patients by means of proADM, whereby a determination of the marker pro-adrenomedullin or partial sequence or a fragment thereof or contained in a marker combination (panel, cluster) is carried out on a post-myocardial infarction patient. The invention also provides a diagnostic device and a kit for the performance of the method of the method of the invention.

18 Claims, 7 Drawing Sheets

Figure 1

SEQ ID No. 1:

```
Met Lys Leu Val Ser Val Ala Leu Met Tyr Leu Gly Ser Leu Ala Phe
 1            5                    10                  15
Leu Gly Ala Asp Thr Ala Arg Leu Asp Val Ala Ser Glu Phe Arg Lys
            20                  25              30
Lys Trp Asn Lys Trp Ala Leu Ser Arg Gly Lys Arg Glu Leu Arg Met
        35              40              45
Ser Ser Ser Tyr Pro Thr Gly Leu Ala Asp Val Lys Ala Gly Pro Ala
    50              55              60
Gln Thr Leu Ile Arg Pro Gln Asp Met Lys Gly Ala Ser Arg Ser Pro
65              70              75                          80
Glu Asp Ser Ser Pro Asp Ala Ala Arg Ile Arg Val Lys Arg Tyr Arg
            85              90              95
Gln Ser Met Asn Asn Phe Gln Gly Leu Arg Ser Phe Gly Cys Arg Phe
            100             105                 110
Gly Thr Cys Thr Val Gln Lys Leu Ala His Gln Ile Tyr Gln Phe Thr
        115             120             125
Asp Lys Asp Lys Asp Asn Val Ala Pro Arg Ser Lys Ile Ser Pro Gln
    130             135                 140
Gly Tyr Gly Arg Arg Arg Arg Ser Leu Pro Glu Ala Gly Pro Gly
145             150             155                         160
Arg Thr Leu Val Ser Ser Lys Pro Gln Ala His Gly Ala Pro Ala Pro
            165             170                 175
Pro Ser Gly Ser Ala Pro His Phe Leu
            180             185
```

Amino acids 1-185 preproADM (185 amino acids)

Amino acids 22-185 proADM (164 amino acids)

Amino acids 95-146 ADM (52 amino acids)

Figure 2

SEQ ID No. 2

```
Glu Leu Arg Met Ser Ser Ser Tyr Pro Thr Gly Leu Ala Asp Val Lys
1               5               10                  15

Ala Gly Pro Ala Gln Thr Leu Ile Arg Pro Gln Asp Met Lys Gly Ala
            20              25                  30

Ser Arg Ser Pro Glu Asp Ser Ser Pro Asp Ala Ala Arg Ile Arg Val
        35              40                  45
```

1-48 MR-proADM = Amino acids 45 – 92 from preproADM (48 amino acids)

SEQUENCE LISTING

<160> NUMBER OF SEQ ID NOS: 2

<210> SEQ ID NO 1
<211> LENGTH: 185
<212> TYPE: PRT

```
<213> ORGANISM: Homo sapiens

<400> SEQUENCE: 1

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
                100                 105                 110

Gly Thr Cys Thr Val Gln Lys Leu Ala His Gln Ile Tyr Gln Phe Thr
            115                 120                 125

Asp Lys Asp Lys Asp Asn Val Ala Pro Arg Ser Lys Ile Ser Pro Gln
        130                 135                 140

Gly Tyr Gly Arg Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 2
<211> LENGTH: 48
<212> TYPE: PRT
<213> ORGANISM: Homo sapiens

<400> SEQUENCE: 2

Glu Leu Arg Met Ser Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
            20                  25                  30

Ser Arg Ser Pro Glu Asp Ser Ser Pro Asp Ala Ala Arg Ile Arg Val
        35                  40                  45
```

METHODS OF DIAGNOSIS AND RISK STRATIFICATION OF ADVERSE EVENTS IN POST MYOCARDIAL INFARCTION PATIENTS USING PRO-ADRENOMEDULLIN

REFERENCE TO RELATED APPLICATIONS

This application claims the benefit of U.S. Provisional Application No. 60/858,083 filed Nov. 9, 2006, which is incorporated herein by reference.

FIELD OF THE INVENTION

The invention relates to a method for the diagnosis and/or risk stratification of adverse events in post-myocardial infarction patients, whereby a determination of the marker pro-adrenomedullin (proADM) or a partial sequence or fragment thereof or contained in a marker combination (panel, cluster) is carried out on a patient who is to be examined.

BACKGROUND OF THE INVENTION

The diagnosis and risk stratification of adverse events (death, heart attack, heart failure) in post-myocardial infarction patients have been described in conjunction with natriuretic proteins, namely, BNP and NTproBNP (Richards A. M., Nicholls M. G., Yandle T. O., Frampton C., Espiner E. A., Turner J. G., Buttimore R. C., Lainchbury J. G., Elliott J. M., Ikram H., Crozier I. G., Smyth D. W. Plasma N-terminal pro-brain natriuretic peptide and adrenomedullin: new neurohormonal predictors of left ventricular function and prognosis after myocardial infarction. Circulation 1998; 97:1921-1929; Squire I. B., O'Brien R. J., Demme B., Davies J. E., Ng L. L. N-terminal pro-atrial natriuretic peptide (N-ANP) and N-terminal pro-B-type natriuretic peptide (N-BNP) in the prediction of death and heart failure in unselected patients following acute myocardial infarction. Clin. Sci. (London) 2004; 107:309-316). However, it is particularly difficult to make a reliable diagnosis or to undertake a stratification in such post-myocardial infarction patients, especially as far as further clinical decisions are concerned.

Moreover, the state of the art describes pro-adrenomedullin (proADM) determination within the scope of the diagnosis (EP 0622458 B1), particularly for purposes of examining sepsis (EP 1121600 B1).

Circulating natriuretic peptide levels such as N-terminal pro B type natriuretic peptide (NTproBNP) provide prognostic information in patients at predicting death and heart failure in the post acute myocardial infarction (AMI) phase.[1] The challenge remains to try and identify those patients who are deemed to be at high risk of adverse events. The addition of biomarkers in risk stratification has been shown to be superior to clinical features at predicting adverse outcomes and this has also been borne out in a range of acute coronary syndromes.[2] Newer peptides are emerging which may give complementary and additional information, particularly in a multi-marker strategy with NTproBNP. Adrenomedullin (ADM) is a 52 amino acid peptide which has homology with calcitonin gene related peptide.[3] It was originally isolated from human pheochromocytoma cells, however it has been detected in other tissues including adrenal medulla, heart, brain, lung, kidney, and gastrointestinal organs[3,4] and its mRNA is highly expressed in endothelial cells.[5] The downstream actions of ADM are mediated by an increase in cAMP levels.[6]

ADM is synthesized as part of a larger precursor molecule, termed preproadrenomedullin. In humans this precursor consists of 185 amino acids.[7] The gene encoding preproadrenomedullin is termed the ADM gene and has been mapped and localized to chromosome 11.[8] ADM is difficult to measure in plasma as it can act in an autocrine or paracrine way, is partially complexed with complement factor H, and is rapidly cleared from the circulation.[9] Recently, the more stable midregional fragment of pro-adrenomedullin (MR-proADM), comprising amino acids 45-92 of preproADM, has been identified which is more stable than the active molecule being secreted in equimolar amounts to adrenomedullin.[10]

The biological activity of ADM in the cardiovascular system is similar to that of B-type natriuretic peptide (BNP) causing vasodilation[11] via production of NO[12] increasing cardiac output[13] and inducing diuresis and natriuresis.[14] Plasma ADM is increased in heart failure, in proportion to the severity of disease[15,16] and is inversely related to LVEF.

Plasma ADM has been investigated previously in two small studies as a prognostic marker comparing it to NTproBNP and BNP.[1,17] One study identified plasma ADM as an independent predictor of cardiogenic shock and short term mortality[17], whereas ADM had no independent additional prognostic value to NTproBNP in another[1].

It is an object of the present invention to provide an improved method for the diagnosis and risk stratification of adverse events in post-myocardial infarction patients.

SUMMARY OF THE INVENTION

This objective is achieved by a method for in-vitro diagnosis and/or risk stratification of adverse events in post-myocardial infarction patients, whereby a determination of the marker pro-adrenomedullin or a partial sequence or fragment thereof or contained in a marker combination (panel, cluster) is carried out on a patient who is to be examined.

Thus, one embodiment of the invention provides a method for the in vitro diagnosis and/or risk stratification of an adverse event in post-myocardial infarction patients, comprising the step of determining the level of pro-adrenomedullin or partial peptides or fragments thereof from a post-myocardial infarction patient, wherein a significantly elevated level of pro-adrenomedullin correlates with a greater risk of an adverse event in said post-myocardial infarction patient. Preferably, the method determines the level of a fragment of pro-adrenomedullin, MR-proADM (SEQ ID No. 2). In preferred embodiments of the invention, adverse event is at least one of myocardial infarction, heart failure and death. The method of the invention can further comprise the step of determining the level of at least one marker selected from the group consisting of BNP, proBNP, NT-proBNP or a partial sequence thereof in each case, from the post-myocardial infarction patient. The method of the invention can also further comprise the step of determining the level of at least one marker selected from the group consisting of inflammatory markers, cardiovascular markers, neurohormonal markers or ischemic markers from said post-myocardial infarction patient.

Preferably, the determination is made in at least one specimen from the post-myocardial infarction patient.

Another embodiment of the invention provides a kit for the in vitro diagnosis and/or risk stratification of an adverse event in post-myocardial infarction patients, containing detection reagents for the determination of the marker pro-adrenomedullin or partial peptides or fragments thereof or contained in a marker combination, whereby the marker combination can contain additional markers as well as an auxiliary agent.

BRIEF DESCRIPTION OF THE FIGURES

FIG. 1 shows the amino acid sequence of preproADM (amino acids 1-185); proADM (amino acids 22-185; 164 amino acids) and ADM (amino acids 95-146; 52 amino acids).

FIG. 2 shows the amino acid sequence of mid-regional pro-adrenomedullin (MR-proADM), which corresponds to amino acids 45-92 of preproADM shown in SEQ ID NO: 1.

DETAILED DESCRIPTION OF THE INVENTION

Figure 3:
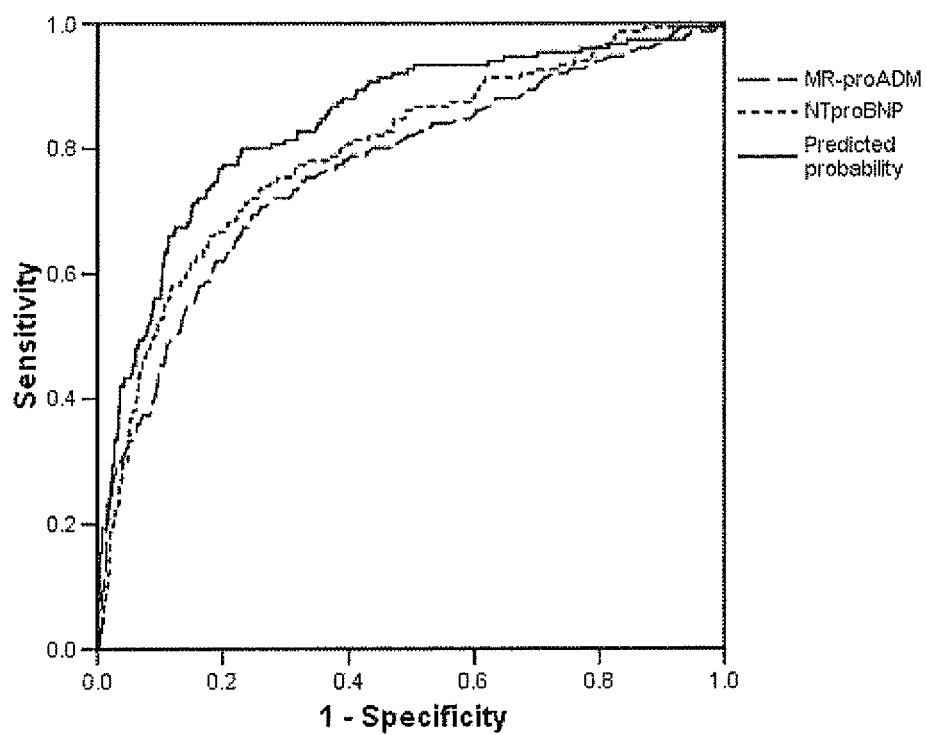
FIG. 3 shows a combined Receiver Operating Characteristic Curve comparing NTproBNP, MR-proADM and the combined predicted probabilities from a binary logistic model for prediction of death or heart failure.

The role of the more stable prohormone MRproADM in the prognostication of AMI was unknown prior to the studies of the present invention, in which the inventors investigated whether MR-proADM would be of benefit in determining the prognosis following AMI, particularly for predicting death and heart failure. The results were compared with NTproBNP, a peptide of established prognostic value in this group of patients.[1,18,19]

According to the invention, the term "risk stratification" comprises the identification of post-myocardial infarction patients, especially emergency patients and risk patients, who display a worse prognosis, for purposes of obtaining a more thorough diagnosis and (follow-up) therapy or treatment with the objective of attaining the most favorable possible outcome for the heart disease.

Consequently, especially in cases of emergency and/or intensive medical care, the method according to the invention is particularly advantageous for obtaining a reliable diagnosis and/or risk stratification. The method according to the invention allows clinical decisions that lead to a fast therapy success. Such clinical decisions likewise comprise further treatment by means of drugs for the treatment or therapy of myocardial infarction or heart failure.

In another preferred embodiment of the method according to the invention, the diagnosis and/or risk stratification is carried out to obtain a prognosis, a prophylaxis, a differential-diagnostic early detection and recognition, an evaluation of the severity and an outcome assessment of an adverse event in post-myocardial infarction patients during their therapy.

In another embodiment of the method according to the invention, blood—optionally whole blood, serum or available plasma—is drawn from the patient who is to be examined and the diagnosis is made in vitro/ex vivo, that is to say, outside of the human or animal body. The diagnosis and/or risk stratification can be made on the basis of the determination of the marker pro-adrenomedullin or partial peptides or fragments thereof and the amount present in at least one specimen from the patient.

Within the scope of this invention, the term "adverse (negative) event in post-myocardial infarction patients" refers especially to another (subsequent) myocardial infarction, heart failure or the occurrence of death or other deterioration of the prognosis of the patient.

Within the scope of this invention, the term "myocardial infarction" (heart attack, acute myocardial infarction—AMI) refers to acute and life-threatening heart disease, whereby necrosis or tissue death (infarction) of parts of the heart muscle (myocardium) occur due to impaired perfusion (ischemia) lasting, as a rule, more than 20 minutes. The cardinal symptom of heart attack is the sudden occurrence of usually strong pain in the chest area (chest pain) that lasts more than 20 minutes and that can radiate into the shoulders, arms, lower jaw and epigastric region and that can be accompanied by sweating, nausea and possibly vomiting. Heart failure is possible as a result of a myocardial infarction.

The term "post-myocardial infarction patient" means that this patient has already suffered a myocardial infarction in the past, that is to say, for instance, more than 1 hour, especially more than 20 hours, especially 1 to 5 days or 3 to 5 days ago, and is now in the post-phase and who did not die immediately, but for whom another adverse event can be expected either directly or indirectly.

All of the above-mentioned indications are also described, for example, in Pschyrembel, published by de Gruyter, Berlin, Germany 2004.

Within the scope of this invention, the term "pro-adrenomedullin proADM)" refers to a human protein or polypeptide with an amino acid sequence of 22-185 (position 22 is Ala, position 185 is Leu) of SEQ ID No. 1 (FIG. 1) of the pre-pro-adrenomedullin (Kitamura K., Sakata J., Kangawa K., Kojima M., Matsuo H., Eto T. Cloning and characterization of cDNA encoding a precursor for human adrenomedullin, Biochem. Biophys. Res. Commun. 1993; 194:720-725) as well as its fragments and partial peptides, especially an amino acid sequence of 95-146 (position 95 is Tyr and position 146 is Tyr) of SEQ ID No. 1 (FIG. 1) of the pre-pro-adrenomedullin, namely, adrenomedullin or an amino acid sequence of 45-92 (position 45 is Glu and position 92 is Val) of SEQ ID No. 1 (FIG. 1) of pre-pro-adrenomedullin or amino acid sequence 1-48 of SEQ ID No. 2 (FIG. 2). This fragment is also referred to as mid-regional pro-adrenomedullin (MR-proADM) (EP 1488209 B1) and, according to the invention, it constitutes an especially preferred fragment because of its high plasma stability. Likewise preferred are those fragments of pro-adrenomedullin that have an N-terminal cleavage of amino acids (so-called NT-proADM), whereby the first 5, 10, 15 or 20 amino acids of the proADM of the N-terminus (starting at position 22 of SEQ ID No. 1) have been deleted (also see EP 0622458 B1). Therefore, partial peptides according to the invention can be the pro-adrenomedullin N-terminal 20-peptide (PAMP), which exhibits hypotensive properties, that is to say, it lowers the blood pressure. A less thoroughly studied C-terminal partial peptide—referred to as adrenotensin—consisting of 33 amino acids (amino acids 153-185 of the preproADM (SEQ ID No. 1)) is encompassed according to the invention. Moreover, the pro-adrenomedullin according to the invention can exhibit posttranslational modifications such as glycolization, lip(o)idization or derivatizations.

In another embodiment, the determination of pro-adrenomedullin can be additionally carried out with other markers, whereby pro-adrenomedullin is contained in a marker combination (panel, cluster), namely, preferably those that already indicate heart disease, especially myocardial infarction.

For this reason, the invention relates to an embodiment of the method according to the invention in which the determination is additionally carried out on a patient who is to be examined with at least one additional marker selected from the group of inflammatory markers, cardiovascular markers, neurohormonal markers or ischemic markers.

According to the invention, the inflammatory marker can be selected from at least one marker from the group of C-reactive protein (CRP), cytokines such as, for instance, TNF alpha (tumor necrosis factor-alpha), interleukins such as IL-6, procalcitonin (1-116, 3-116) and adhesion molecules such as VCAM or ICAM, as well as the cardiovascular markers from at least one marker selected from the group consisting of creatine kinase, myeloperoxidase, myoglobin, natriuretic protein, especially ANP (or ANF), proANP, NT-proANP, BNP, proBNP, NT-proBNP or a partial sequence thereof in each case, cardial troponin, CRP. Moreover, this also refers to circulation-regulating (pro)hormones, particularly such as pro-gastrin-releasing peptide (proGRP), pro-endothelin-1, pro-leptin, pro-neuropeptide-Y, pro-somatostatin, pro-neuropeptide-YY, pro-opiomelanocortin or a partial sequence thereof in each case.

The ischemic marker can be selected from at least one marker from the group consisting of troponin I and T, CK-MB. Moreover, the neurohormonal marker can be at least one natriuretic protein, especially ANP (or ANF), proANP, NT-proANP, BNP, proBNP, NT-proBNP or a partial sequence thereof in each case.

In a very especially preferred embodiment, the additional marker is BNP, proBNP, NT-proBNP (for markers associated with BNP, see: Tateyama et al., Biochem. Biophys. Res. Commun. 185: 760-7 (1992); Hunt et al., Biochem. Biophys. Res. Commun. 214: 1175-83 (1995)) or a partial sequence thereof in each case.

Particularly in the examples, it is demonstrated that a marker combination of the marker according to the invention, namely, pro-adrenomedullin, and NT-proBNP, has greater significance for the diagnosis and/or risk stratification of post-myocardial infarction patients in terms of an adverse event (outcome) at the given endpoints.

In another embodiment of the invention, this preferred combination, in turn, can be augmented by additional markers mentioned here to form a marker combination (panel, cluster).

In another embodiment of the invention, the method according to the invention can be carried out by means of parallel or simultaneous determinations of the markers (e.g. multititer plates with 96 or more cavities), whereby the determinations are made in at least one specimen from a patient.

Moreover, the method according to the invention and its determinations can be carried out in an automatic analysis device, especially by means of a KRYPTOR automatic analysis device.

In another embodiment, the method according to the invention and its determinations can be carried out by means of a quick test (for example, lateral-flow test), whether it is in a single-parameter or multi-parameter determination.

Moreover, the invention relates to the use of pro-adrenomedullin or partial peptides or fragments thereof or contained in a marker combination (panel, cluster) for the in vitro diagnosis and/or risk stratification of an adverse event in post-myocardial infarction patients, especially taking into consideration the above-mentioned embodiments.

Another objective is to provide a corresponding diagnostic device or the use of such a device for carrying out the method according to the invention. Within the scope of this invention, such a diagnostic device refers to an array or assay (for instance, immunoassay, ELISA, etc.), in the broadest sense, to a device for carrying out the method according to the invention.

The invention also relates to a kit or to the use of such a kit for in vitro diagnosis and risk stratification of an adverse event in post-myocardial infarction patients, whereby a determination of pro-adrenomedullin or partial peptides or fragments thereof or contained in a marker combination (panel, cluster) is carried out on a patient who is to be examined, especially taking into consideration the above-mentioned embodiments. Such detection reagents comprise, for instance, antibodies, etc.

The examples and figures below serve to elucidate the invention in greater detail without, however, limiting the invention to these examples and figures.

EXAMPLE

Study Population

The study population was 983 consecutive acute myocardial infarction patients admitted to the Coronary Care Unit of Leicester Royal Infirmary. The study complied with the Declaration of Helsinki and was approved by the local ethics committee; written informed consent was obtained from patients. AMI was defined at presentation with at least two of three standard criteria, i.e. appropriate symptoms, acute ECG changes of infarction (ST elevation or depression, new left bundle branch block) and a rise in troponin T above the $99^{th}$ percentile for our population. AMI was sub-categorised into ST segment elevation myocardial infarction (STEMI) or non-ST segment myocardial infarction (NSTEMI). Exclusion criteria were known malignancy, or surgery in the previous month.

Plasma Samples

Blood samples were drawn at 3 to 5 days after the onset of chest pain for determination of plasma MR-proADM and NTproBNP. After 15 minutes bed rest, 20 mL blood was collected into tubes containing EDTA and aprotinin. All plasma was stored at −70° C. until assayed in a blinded fashion in a single batch.

Echocardiography

Transthoracic echocardiography was performed in patients using a Sonos 5500 instrument (Philips Medical Systems, Reigate, UK). A 16-segment left ventricular wall motion index (LVWMI) based on the American Society of Echocardiography mode was derived by scoring each LV segment (1=normal, 2=hypokinesis, 3=akinesis and 4=dyskinesis (Paradoxical Motion), and dividing the total by the number of segments scored. Left ventricular ejection fraction (LVEF) was calculated using the biplane method of discs formula.[20] Impaired LV systolic function was defined as an EF<40% or a LVWMI>1.8.

NTproBNP Assay

The NTproBNP assay was based on a non-competitive assay as previously published.[2] Sheep antibodies were raised to the N-terminal of human NTproBNP and monoclonal mouse antibodies were raised to the C-terminal. Antibodies raised against the N-terminal were affinity-purified and biotinylated. Samples or NTproBNP standards were incubated in C-terminal IgG-coated wells with the biotinylated N-terminal antibody for 24 hours at 4° C. Detection was with methyl-acridinium ester (MAE)-labelled streptavidin on a MLX plate luminometer (Dynex Technologies Ltd., Worthing, UK). The lower limit of detection was 0.3 pmol/L. There was no cross reactivity with atrial natriuretic peptide, BNP, or C-type natriuretic peptide.

MR-proADM Assay

MR-proADM was detected using a novel commercial assay in the chemiluminescence/coated tube-format (BRAHMS AG) as described in Morgenthaler N G, Struck J, Alonso C, Bergmann A. Measurement of midregional proadrenomedullin in plasma with an immunoluminometric assay. Clin Chem. 51(10):1823-9, October 2005). Briefly, tubes were coated with a purified sheep polyclonal antibody raised against a peptide representing amino acids 83-94 of preproADM. A purified sheep polyclonal antibody raised against a peptide representing amino acids 68-86 of preproADM was labelled with MACN-Acridinium-NHS-Ester (InVent GmbH, Germany) and used as tracer. Dilutions of a peptide representing amino acids 45-92 of preproADM in normal horse serum served as standards. The immunoassay was performed by incubating 10 µl of samples/standards and 200 µl tracer in coated tubes for 2 h at room temperature. Tubes were washed 4 times with 1 ml of LIA wash solution (BRAHMS AG), and bound chemiluminescence was measured using a LB952T luminometer (Berthold, Germany).

End Points

The value of both MR-proADM and NTproBNP were assessed for the prediction of death and heart failure. The combined primary endpoint consisted of death and heart failure. Death, heart failure and recurrent AMI were also investigated as individual secondary endpoints. Myocardial infarction (MI) was diagnosed if a patient had chest pain lasting >20 minutes, diagnostic serial electrocardiographic (ECG) changes consisting of new pathological Q waves or ST-segment and T-wave changes, and a plasma creatine kinase-MB elevation greater than twice normal or cardiac troponin I level>0.1 ng/mL.[21] Hospitalization for heart failure was defined as a hospital admission for which heart failure was the primary reason. Endpoints were obtained by reviewing the Office of National Statistics Registry and by contacting each patient. There was a minimum 30-day follow-up of all surviving patients.

Statistical Analysis

Statistical analyses were performed on SPSS Version 12 (SPSS Inc, Chicago, Ill.). The continuous variables in the two independent groups were compared using the Mann Whitney U test. To test the independent predictive power for death or heart failure of peptides levels above and below the median, Spearman's correlations were performed and binary logistic regression analyses were conducted. Baseline patient characteristics (age, sex, serum creatinine, Killip class, and territory of AMI) and peptide markers (including troponin I) were included as variables. Levels of NTproBNP and MR-proADM were normalised by log transformation. Thus, odds ratios and hazard ratios refer to a tenfold rise in the levels of these markers.

To compare the predictive value of NTproBNP, MR-proADM or the predicted probability derived from logistic regression analyses, receiver-operating characteristic (ROC) curves were generated and the area under the curves (AUC) was calculated. To identify the independent predictors of death or heart failure, Cox proportional hazard analyses was used. Kaplan Meier survival curves were generated to visualise the relationship between the peptides NTproBNP and MR-proADM and the primary and secondary endpoints. A p value of less than 0.05 was deemed to be statistically significant.

Results

Patient Characteristics

The demographic features of the patient population are shown in Table 1. Median length of follow-up was 342 days with a range of 0-764 days. No patient was lost to follow-up. During follow-up, 101 (10.3%) patients died and 49 (5.0%) were readmitted with heart failure. There were 784 STEMI patients, 67.8% of whom were thrombolysed. Echocardiographic data was available for 645 (65.6%) of the 983 patients and done during index admission.

TABLE 1

Characteristics of the 983 patients in the study separated by MR-proADM quartiles. Values are means (SD) or numbers (%)

|  | 1st quartile | 2nd quartile | 3rd quartile | 4th quartile | p value |
|---|---|---|---|---|---|
| Age (in years) | 55.5 ± 10.7 | 63.5 ± 10.1 | 67.4 ± 10.3 | 73.6 ± 10.1 | <0.001 |
| Previous Medical History |  |  |  |  |  |
| AMI | 25 (10.2) | 37 (15.0) | 43 (17.5) | 59 (24.1) | <0.0001 |
| Angina Pectoris | 52 (21.1) | 57 (23.2) | 68 (27.6) | 72 (29.4) | 0.150 |
| Hypertension | 80 (32.5) | 105 (42.7) | 108 (43.9) | 126 (51.4) | <0.0001 |
| Diabetes mellitus | 31 (12.6) | 53 (21.5) | 43 (17.5) | 88 (35.9) | <0.001 |
| High cholesterol | 51 (20.7) | 56 (22.8) | 59 (24.0) | 58 (23.7) | 0.843 |
| Current/Ex-Smokers | 166 (67.5) | 153 (62.2) | 146 (59.3) | 140 (57.1) | 0.06 |
| ST-elevation AMI | 187 (76.0) | 200 (81.3) | 205 (83.3) | 201 (82.0) | 0.244 |
| Thrombolytic | 136 (55.3) | 131 (53.3) | 146 (59.3) | 111 (45.3) | 0.043 |
| Territory of Infarct |  |  |  |  | 0.320 |
| Anterior | 108 (43.9) | 106 (43.1) | 95 (38.6) | 101 (41.2) |  |
| Inferior | 100 (40.7) | 86 (35.0) | 103 (41.9) | 85 (34.7) |  |
| Other | 37 (15.1) | 54 (22.0) | 48 (19.5) | 60 (24.5) |  |
| Killip Class on Admission |  |  |  |  | <0.001 |
| I | 165 (67.0) | 134 (54.5) | 114 (46.3) | 74 (30.2) |  |
| II | 63 (25.6) | 94 (38.2) | 104 (42.3) | 114 (46.5) |  |
| III | 10 (4.1) | 9 (3.7) | 22 (8.9) | 47 (19.2) |  |
| IV | 1 (0.4) | 0 (0) | 0 (0) | 9 (3.7) |  |
| Peak CK (IU/L) | 955.1 ± 1054.6 | 1041.9 ± 1152.9 | 1063.8 ± 1124.3 | 1210.7 ± 1427.9 | 0.142 |
| Creatinine (µmol/L) | 91.0 ± 17.6 | 91.3 ± 18.2 | 101.9 ± 26.0 | 125.6 ± 48.9 | <0.001 |
| NTproBNP (pmol/L) | 1004.2 ± 2168.6 | 1344.8 ± 1780.8 | 1923.1 ± 2228.9 | 4195.2 ± 3721.5 | <0.001 |
| Male Sex | 211 (85.8) | 178 (72.3) | 177 (72.0) | 146 (59.6) | <0.0001 |

TABLE 2

Multivariate Cox proportional hazards regression model of significant predictors of death or heart failure

| Variable | Hazard Ratio | 95% CI | p value |
|---|---|---|---|
| Log MR-proADM | 3.63 | 1.48-8.90 | 0.005 |
| Log NTproBNP | 2.67 | 1.82-3.90 | 0.0001 |
| Age | 1.03 | 1.02-1.05 | 0.0001 |
| Sex | 0.69 | 0.46-0.96 | 0.031 |
| PMH of AMI | 1.76 | 1.24-2.50 | 0.001 |
| Log creatinine | 4.05 | 0.99-16.67 | 0.052 |

MR-proADM Levels in Patients

Plasma levels of MR-proADM in patients with AMI ranged from 0.09-6.66 nmol/L with a median of 0.73 nmol/L, being elevated compared to the established normal range (mean 0.33, range 0.10-0.64 nmol/L).[10] MR-proADM was significantly higher in patients who died (1.31; [0.09-5.39] vs. 0.71; [0.25-6.66] nmol/L; $p<0.0001$) or were readmitted with heart failure (1.10; [0.40-4.39] vs. 0.71; [0.25-6.66] nmol/L; $p<0.0001$) compared to event free survivors. There was a significantly higher level in females compared with males ($p<0.0001$), in patients with a PMH of AMI ($p<0.0001$), in those with a history of hypertension ($p<0.0001$) and in patients who had a past history of heart failure ($p=0.001$). MR-proADM levels were not significantly different between STEMI and NSTEMI patients. MR-proADM was lower in patients who were thrombolysed ($p=0.043$).

There was correlation of MR-proADM with age ($r_s=0.552$, $p<0.0001$), log creatinine ($r_s=0.404$, $p<0.0001$), Killip class ($r_s=0.314$, $p<0.0001$), and NTproBNP ($r_s=0.519$, $p<0.0001$).

NTproBNP Levels in Patients

NTproBNP was significantly higher in patients who died (5929.3; [104.3-16994.2] vs. 839.0; [0.30-28886.8] pmol/L; $p<0.0001$) or were readmitted with heart failure (3932.9; [2.43-12933.0] vs. 839.0; [0.3-28886.8] pmol/L; $p<0.0001$). Significant differences in NTproBNP levels were noted between males and females (788.7; [0.3-28886.8] vs. 1632.6; [5.7-24016.0] pmol/ml; $p<0.0001$) and those with a Killip class above 1 (631.0; [0.3-24016.0] vs. 1583.4; [0.3-28886.8] pmol/ml; ($p<0.0001$) and in patients with a PMH of heart failure (668.6; [5.70-28886.8] vs. 2415.9; [89.6-12933.0] pmol/ml; $p=0.001$) or AMI (844.4; [0.3-28886.8] vs. 1332.3; [0.3-11259.0] pmol/ml; $p=0.03$).

Relationship Between MR-proADM and Echocardiographic Parameters

MR-proADM and NTproBNP were higher in patients with impaired LV systolic function (as defined by EF<40% or LVWMI>1.8 on echocardiography) (median [range] 0.91; [0.25-6.66] vs. 0.69; [0.09-5.57]; nmol/L, $p<0.0001$) and 2286.1; [0.3-16994.2] vs. 804.6; [0.3-28886.8]; pmol/L, $p<0.0001$), respectively.

Primary Endpoints: MR-proADM and NTproBNP as Predictors of Death and Heart Failure MR-proADM was raised in patients with death or heart failure compared to survivors (median [range] nmol/L, 1.19; [0.09-5.39] vs. 0.71; [0.25-6.66]; $p<0.0001$).

When clinical and demographic characteristics (age, sex, PMH of AMI, Killip class, log creatinine, NTproBNP and MR-proADM), were entered into a multivariate binary logistic model MR-proADM (OR 4.22, 95% CI: 1.25-14.26, $p=0.02$) and NTproBNP (OR 3.20, 95% CI: 2.07-4.94, $p<0.0001$) independently predicted the primary endpoint along with age (OR 1.04), gender (OR for male vs female 0.65), PMH of AMI (OR 2.51) and log creatinine (OR 8.25).

The Nagelkerke $r^2$ was 0.35 suggesting a good fit of the model. Killip class was no longer an independent predictor of death and heart failure. The receiver-operating-characteristic curve for MR-proADM yielded an area under the curve (AUC) of 0.77 (95% CI: 0.72-0.81, $p<0.001$); for NTproBNP the AUC was 0.79 (95% CI: 0.75-0.84, $p<0.001$). The predicted probability from the binary logistic model combining the 2 markers yielded an AUC of 0.84 (95% CI 0.81-0.88, $p<0.001$), which exceeded that of either peptide alone (FIG. 3).

Cox proportional hazards modelling confirmed that the same variables (namely MR-proADM, NTproBNP, age, gender, PMH of AMI and log creatinine) were independent predictors of death or heart failure (Table 2).

Figure 4:
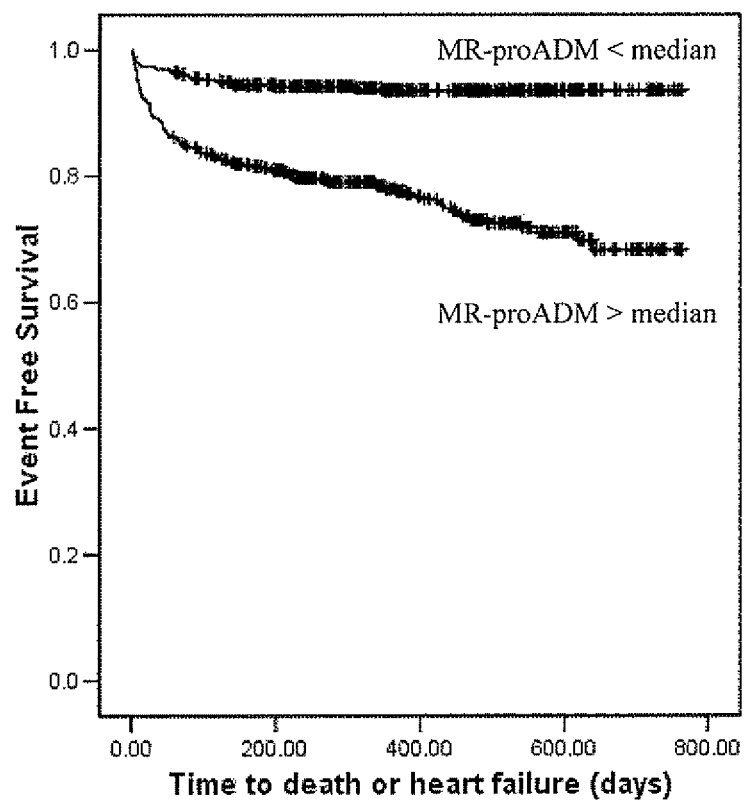
FIG. 4 shows a Kaplan-Meier Curve: Time to death or heart failure related to plasma MR-proADM.
Figure 5:
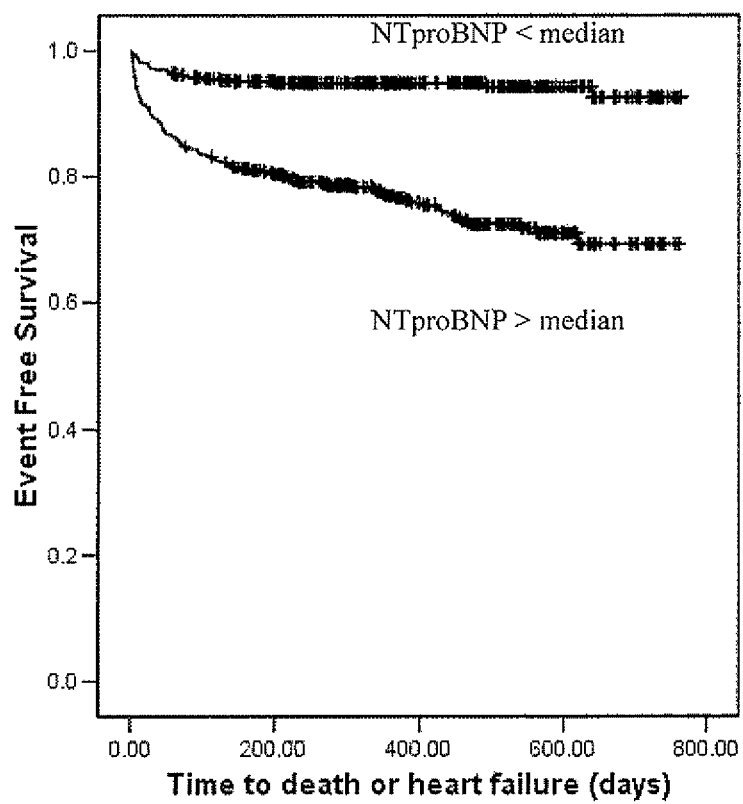
FIG. 5 shows a Kaplan-Meier Curve: Time to death or heart failure related to plasma NTproBNP.
Figure 6:
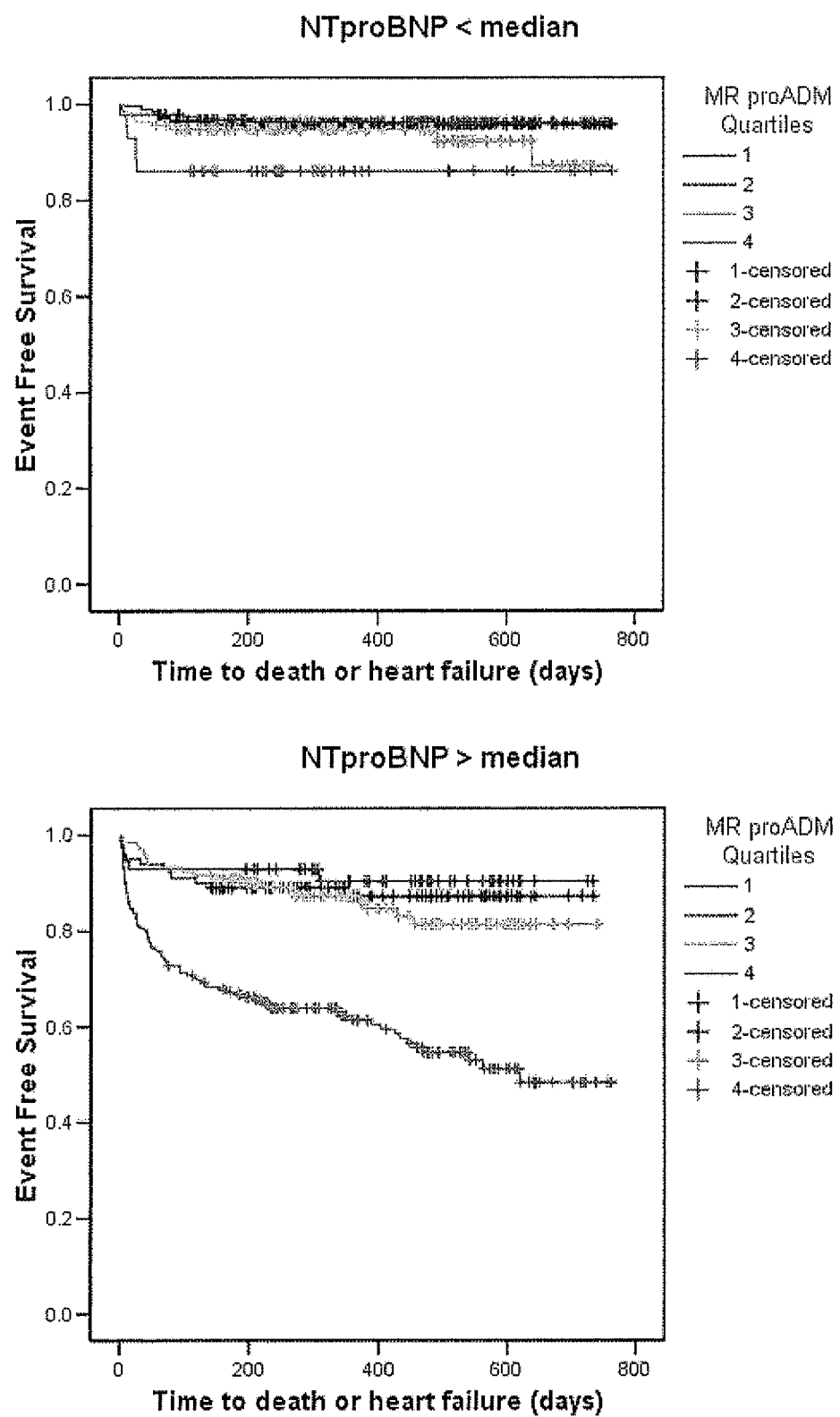
FIG. 6 shows a Kaplan-Meier analysis for quartiles of MR-proADM predicting the primary endpoint of death or heart failure, in patients stratified by NTproBNP (< or > median).

The Kaplan-Meier survival curve revealed a significantly better clinical outcome in patients with MR-proADM below the median (0.73 nmol/L) compared with those with MR-proADM above the median (log rank 61.27, $p<0.0001$, FIG. 4). This was also true for NTproBNP (log rank 68.27, $p<0.0001$, FIG. 5). In patients stratified by NTproBNP (median 914 pmol/L), MR-proADM gave additional information on death and heart failure in those patients who had NTproBNP level above the median (log rank for trend 57.22, $p<0.0001$, FIG. 6), and even for patients below the NTproBNP median value, MR-proADM had some predictive value (log rank for trend 8.72, $p=0.033$, FIG. 6). Patients in the top quartile for MR-proADM (above 1.04 nmol/L) had a significantly higher mortality than those in quartiles 1 to 3 ($p<0.0001$ for all). For NTproBNP below the median, those patients in the top quartile of MR-proADM had higher event rates than those in quartile 1 ($p=0.006$) and 2 ($p=0.018$), (FIG. 6).

Figure 7:
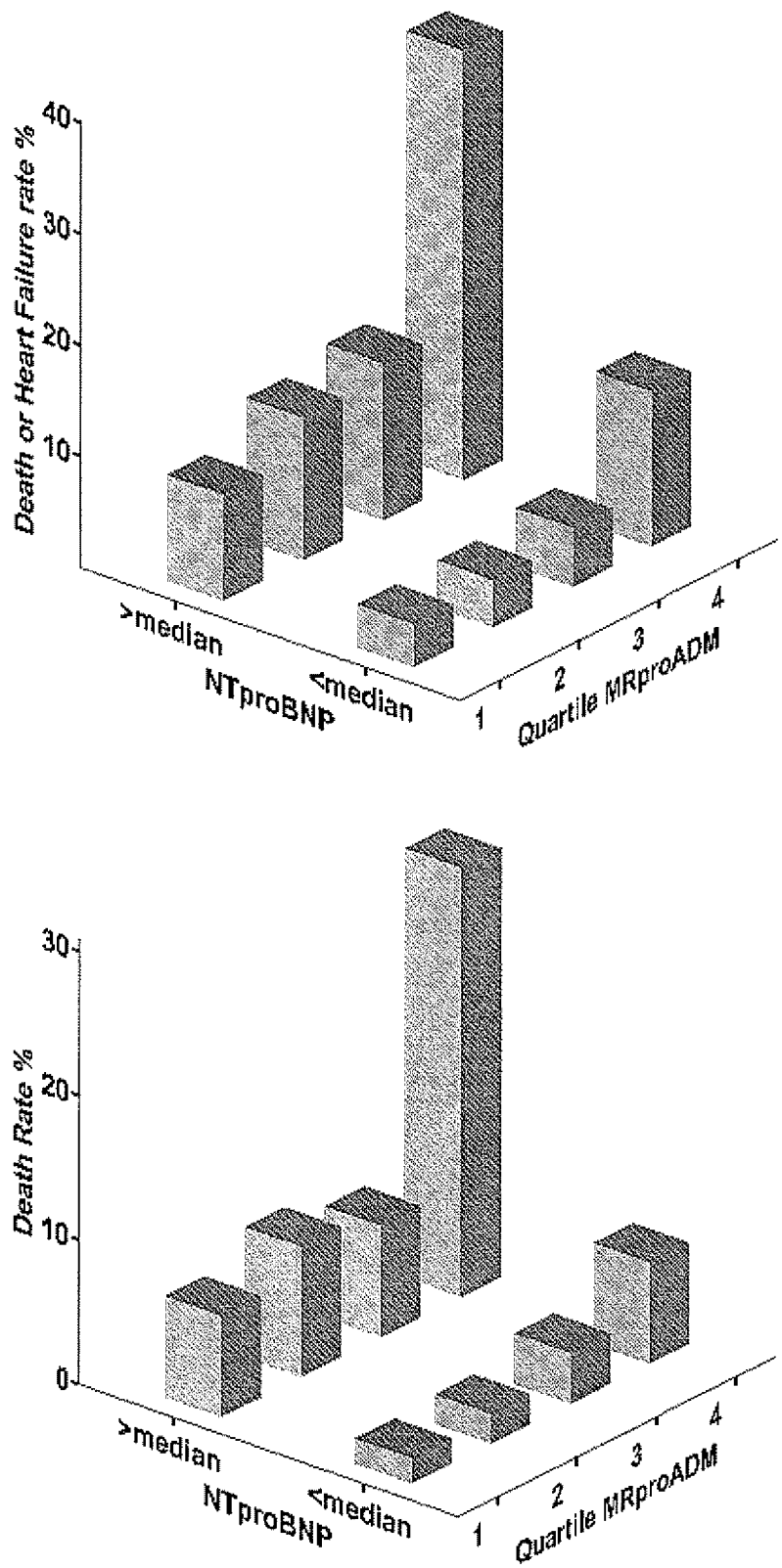
FIG. 7 shows annual event rates for death and for death or heart failure, in patients stratified by NTproBNP (< or > median) and MRproADM quartiles.

The event rates at 1 year for both death and heart failure readmission or death alone in patients stratified by median NTproBNP (914 pmol/L) and quartiles of MR-proADM are illustrated in FIG. 7, in which the top quartile of MR-proADM (1.04 nmol/L) predicted those at highest risk.

Secondary Endpoints: MR-proADM and NTproBNP as Predictors of Death

As described above both markers were significantly raised in patients who died. On Cox proportional hazards modelling the strongest independent predictors of death were MR-proADM (HR 4.86, 95% CI: 1.98-11.95, $p=0.001$) and NTproBNP (HR 3.64, 95% CI:2.20-6.03, $p<0.0001$), the other independent predictors were age (HR 1.06, $p<0.0001$), and PMH of AMI (HR 1.64, $p=0.019$). Kaplan-Meier analysis revealed a significantly better clinical outcome in patients with MR-proADM below the median compared with those with MR-proADM above the median (log rank 42.40, $p<0.0001$). In addition quartiles of MR-proADM predicted those with the highest mortality, stratified by NTproBNP levels above the median (log rank for trend 44.76, $p<0.0001$) and those in the top MR-proADM quartile had higher mortality than those in quartiles 1-3 ($p<0.0005$, $p<0.0001$, $p<0.0001$ respectively).

Secondary Endpoints: MR-proADM and NTproBNP as Predictors of Heart Failure

As described above both markers were significantly raised in patients who were readmitted with heart failure.

On Cox proportional hazards modelling the independent predictors of heart failure were MR-proADM (HR 7.29, 95% CI: 2.45-21.67, $p<0.0001$), NTproBNP (HR 1.71, 95% CI: 1.04-2.81, $p=0.034$), Killip class above 1 (HR 2.04, 95% CI: 1.16-3.59, $p=0.014$), and PMH of AMI (HR 1.93, 95% CI: 1.16-3.19, $p=0.011$).

The Kaplan-Meier survival curve revealed a significantly better clinical outcome in patients with MR-proADM below the median compared with those with MR-proADM above the median (log rank 28.65, p<0.0001). Following stratification by the median NTproBNP level, quartiles of MR-proADM predicted those with the highest readmission rate for heart failure especially in those with NTproBNP above the median (log rank for trend 21.1, p<0.0001) and those in MR-proADM quartiles 2 (p<0.027), 3 (p=0.0008) and 4 (p=0.002) had higher readmission rates for heart failure than those in quartile 1.

Secondary Endpoints: MR-proADM and NTproBNP as Predictors of Myocardial Infarction Compared to survivors with no endpoints, patients who were readmitted with AMI had similar NTproBNP (median [range] 890.4; [0.3-28886] pmol/L vs. 1440.5; [2.6-10646.3]; p=NS) and MRproADM levels (median [range] 0.73; [0.09-6.66] nmol/L vs. 0.75; [0.31-2.00]; p=NS).

Discussion

This is the first report investigating the prognostic potential of MR-proADM in a large cohort of patients from a single centre and comparing this with NTproBNP, a well-established marker of death and heart failure. Our data indicate by survival analysis using both Kaplan-Meier and Cox proportional hazard models that MR-proADM is a powerful independent predictor of death and heart failure, with combined levels of MR-proADM and NTproBSNP giving independent prognostic information. Neither marker, however, was predictive of recurrent myocardial infarction.

Reperfusion therapy and the application of secondary prevention therapies have improved mortality post AMI. Despite this, outcome remains poor for some patients.[22] Risk stratification at an early stage after AMI remains important and may be useful in helping to select treatment regimes or investigation pathways in the future. A multimarker strategy for outcome post-AMI using independent biomarkers has benefits in that it integrates the different pathways involved in the hope that complementary information can be gained.[23] Although from ROC curve analysis, NTproBNP was the more accurate marker for predicting outcome, MR-proADM levels provided complementary prognostic information. The combination of MR-proADM and NTproBNP in a multi-marker risk stratification approach generated an increased area under the ROC curve and greater predictive accuracy. Kaplan-Meier analysis revealed MR-proADM was particularly useful in the in the group of patients who had a raised NTproBNP (above about 900 pmol/L). Levels of MR-proADM were predictive of poor outcome especially in those with levels above the top quartile (1.04 nmol/L). Multivariate analyses (binary and the more statistically powerful Cox regression) demonstrated that MR-proADM and NTproBNP both retained statistically significant power for prediction of death and heart failure independent of other demographic and clinical variables. These findings have been obtained from a heterogeneous AMI population with varying pre morbid cardiovascular disease and variations in the treatments offered to patients particularly with regards to thrombolysis.

The stimuli to the secretion of both markers may be similar; this is backed up by significantly greater values of MR-proADM and NTproBNP in patients with left ventricular systolic dysfunction. In addition, there are similarities in MR-proADM and NTproBNP levels between males and females, (both peptide levels higher in females compared to males) and both levels increase with age from what has been measured so far: Less pronounced for MR-proADM than for NTproBNP.

NTproBNP is a more stable by-product in the production of BNP.[24] In similar fashion MR-proADM is the more stable by-product of ADM released in a 1:1 ratio. The benefit of measuring the prohormones over the active peptide is that the lack of receptor binding or protein interactions and the longer half-lives result in higher plasma levels. The prohormones are also more stable in blood ex-vivo, and this makes them generally more applicable in clinical practice.[10]

ADM may have a number of advantageous effects in the post-AMI period, causing vasodilation (with reduction of arterial and cardiac filling pressures) at a time when the myocardium has been compromised and may cause increased myocardial contractility via its downstream actions on cAMP.[6] ADM may also play a role in maintaining sodium balance, inhibiting the production of aldosterone despite an elevated renin activity, and thereby optimizing cardiac filling at a time when the ventricle has taken an insult.[25]

ADM has been investigated previously in the post AMI period where it was found to be weakly predictive of death.[1] However its independent predictive power was lost for death and heart failure when NTproBNP was evaluated. Interestingly, it was not found to be raised in patients who later died or developed heart failure[1] but this may have been due to the size of population investigated and possibly the fact that ADM has a short half life, and is bound to receptors and other binding proteins.[10] In another study ADM was found to be an independent predictor of death and cardiogenic shock post AMI.[17] ADM has also been shown to be raised in heart failure[16,26] with levels increasing with the severity of NYHA class.[15] The current findings confirm that the ADM system may be another candidate neurohormonal pathway, in addition to the renin-angiotensin and sympathetic nervous systems that may be associated with poor outcome after AMI. The confirmation of the independent predictive value of MR-proADM together with NTproBNP may have been achieved due to the design of the MR-proADM assay which measures prohormone that does not bind to binding proteins or receptors, with a resultant short half life.[10] This further strengthens the concept of measurement of prohormones in disease states, as plasma levels of these biologically inactive fragments are generally higher than the active hormone.

CONCLUSION

Activation of the adrenomedullin system post AMI and MR-proADM is a powerful new prognostic marker of death or heart failure and the combined endpoint of both outcomes, in patients with AMI, independent of established conventional risk factors and newer plasma biomarkers such as NTproBNP. A multimarker approach with MR-proADM and NTproBNP is more informative than either marker alone, and may be useful for risk stratification in AMI patients, with the possibility of changes in the investigation and therapy of such individuals.

All of the references described or referred to herein are incorporated by reference in their entirety for all useful purposes.

While certain specific structures embodying the invention are shown and described, it will be obvious to those skilled in the art that various modifications and rearrangements of the parts may be made without departing from the spirit and scope of the underlying inventive concept and that said invention is not limited to the particular forms shown and described herein.

REFERENCES

1) Richards A M, Nicholls M G, Yandle T G, Frampton C, Espiner E A, Turner J G, Buttimore R C, Lainchbury J G, Elliott J M, Ikram H, Crozier I G, Smyth D W. Plasma N-terminal pro-brain natriuretic peptide and adrenomedul- 1) lin: new neurohormonal predictors of left ventricular function and prognosis after myocardial infarction. Circulation 1998; 97:1921-1929
2) Omland T, Persson A, Ng L, O'Brien R, Karlsson T, Herlitz J, Hartford M, Caidahl K. N-terminal pro-B-type natriuretic peptide and long-term mortality in acute coronary syndromes. Circulation 2002; 106:2913-2918
3) Kitamura K, Kangawa K, Kawamoto M, Ichiki Y, Nakamura S, Matsuo H, Eto T. Adrenomedullin: a novel hypotensive peptide isolated from human pheochromocytoma. Biochem Biophys Res Commun. 1993; 192:553-560.
4) Ichiki Y, Kitamura K, Kangawa K, Kawamoto M, Matsuo H, Eto T. Distribution and characterization of immunoreactive adrenomedullin in human tissue and plasma. FEBS Lett. 1994; 338:6-10.
5) Sugo S, Minamino N, Kangawa K, Miyamoto K, Kitamura K, Sakata J, Eto T, Matsuo H Endothelial cells actively synthesize and secrete adrenomedullin. Biochem Biophys Res Commun 1994; 201:1160-1166.
6) Takahashi K, Satoh F, Hara E, Sone M, Murakami O, Kayama T, Yoshimoto T, Shibahara S Production and secretion of adrenomedullin from glial cell tumors and its effects on cAMP production. Peptides 1997; 18:1117-1124.
7) Kitamura K, Sakata J, Kangawa K, Kojima M, Matsuo H, Eto T. Cloning and characterization of cDNA encoding a precursor for human adrenomedullin Biochem Biophys Res Commun 1993; 194:720-725.
8) Ishimitsu T, Kojima M, Kangawa K, Hino J, Matsuoka H, Kitamura K, Eto T, Matsuo H Genomic structure of human adrenomedullin gene. Biochem Biophys Res Commun 1994; 203:631-639.
9) Hinson J P, Kapas S, Smith D M: Adrenomedullin, a multifunctional regulatory peptide. Endocr Rev 2000; 21:138-167.
10) Morgenthaler N G, Struck J, Alonso C, Bergmann A. Measurement of midregional proadrenomedullin in plasma with an immunoluminometric assay. Clin Chem 2005; 51: 1823-1829.
11) Nakamura M, Yoshida H, Makita S, Arakawa N, Niinuma H, Hiramori K. Potent and long-lasting vasodilatory effects of adrenomedullin in humans. Comparisons between normal subjects and patients with chronic heart failure. Circulation 1997; 95:1214-1221.
12) Parkes D G, May C N. ACTH-suppressive and vasodilator actions of adrenomedullin in conscious sheep. J Neuroendocrinol 1995; 7:923-929
13) Parkes D G, May C N. Direct cardiac and vascular actions of adrenomedullin in conscious sheep. Br J Pharmacol. 1997; 120:1179-1185.
14) Vari R C, Adkins S D, Samson W K. Renal effects of adrenomedullin in the rat. Proc Soc Exp Biol Med 1996; 211:178-183.
15) Jougasaki M, Rodeheffer R J, Redfield M M, Yamamoto K, Wei C-M, McKinley L J, Burnett J C. Cardiac secretion of adrenomedullin in human heart failure. J Clin Invest. 1996; 97:2370-2376.
16) Kato J, Kobayashi K, Etoh T, Tanaka M, Kitamura K, Imamura T, Koiwaya Y, Kangawa K, Eto T. Plasma adrenomedullin concentration in patients with heart failure. J Clin Endocrinol Metab. 1996; 81:180-183.
17) Katayama T, Nakashima H, Furudono S, Honda Y, Suzulci S, Yano K. Evaluation of neurohumoral activation (adrenomedullin, BNP, catecholamines, etc.) in patients with acute myocardial infarction. Intern Med. 2004; 43:1015-1022.
18) Omland T, de Lemos J A, Morrow D A, et al. Prognostic value of N-terminal pro-atrial and pro-brain natriuretic peptide in patients with acute coronary syndromes. Am J Cardiol 2002; 89:463-450.
19) Squire I B, O'Brien R J, Demme B, Davies J E, Ng L L. N-terminal pro-atrial natriuretic peptide (N-ANP) and N-terminal pro-B-type natriuretic peptide (N-BNP) in the prediction of death and heart failure in unselected patients following acute myocardial infarction. Clin Sci (Lond) 2004; 107:309-316.
20) Schiller N B, Shah P M, Crawford M, DeMaria A, Devereux R, Feigenbaum H, Gutgesell H, Reichek N, Sahn D, Schnittger I, et al. Recommendations for quantitation of the left ventricle by two-dimensional echocardiography. American Society of Echocardiography Committee on Standards, Subcommittee on Quantitation of Two-Dimensional Echocardiograms. J Am Soc Echocardiogr 1989; 2:358-367.
21) Alpert J S, Thygesen K, Antman E, Bassand J P. Myocardial infarction redefined—a consensus document of The Joint European Society of Cardiology/American College of Cardiology Committee for the redefinition of myocardial infarction. J Am Coll Cardiol. 2000; 36: 959-969
22) Herlitz J, Dellborg M, Karlson B W, Karlsson T. Prognosis after acute myocardial infarction continues to improve in the reperfusion era in the community of Goteborg. Am Heart J 2002; 144:89-94.
23) Sabatine M S, Morrow D A, de Lemos J A, Gibson C M, Murphy S A, Rifai N, McCabe C, Antman E M, Cannon C P, Braunwald E. Multimarker approach to risk stratification in non-ST elevation acute coronary syndromes: simultaneous assessment of troponin I, C-reactive protein, and B-type natriuretic peptide. Circulation 2002; 105:1760-1763.
24) Mueller T, Gegenhuber A, Dieplinger B, Poelz W, Haltmayer M. Long-term stability of endogenous B-type natriuretic peptide (BNP) and amino terminal proBNP (NT-proBNP) in frozen plasma samples. Clin Chem Lab Med 2004; 42:942-944.
25) Rademaker M T, Charles C J, Lewis L K, Yandle T G, Cooper G J S, Coy D H, Richards A M, Nicholls M G. Beneficial hemodynamic and renal effects of adrenomedullin in an ovine model of heart failure. Circulation 1997; 96:1983-1990.
26) Jougasaki, M, Wei C M, McKinley L U, Burnett J C. Elevation of circulating and ventricular adrenomedullin in human congestive heart failure. Circulation 1995 92: 286-289.

What is claimed is:

1. A method for the in vitro diagnosis or risk stratification of an adverse event in post-myocardial infarction patients, comprising
   a) determining the level of MR-proADM (SEQ ID NO: 2) in at least one blood specimen from a post-myocardial infarction patient using an immunoassay and an antibody specific for MR-proADM (SEQ ID NO: 2), and
   b) diagnosing or stratifying the risk of an adverse event in said post-myocardial infarction patient based on the result in a), wherein a level of MR-proADM (SEQ ID NO: 2) of greater than 0.73 nmol/L in said specimen correlates with a greater risk of death of or heart failure in said post-myocardial infarction patient.

2. The method of claim 1, wherein a level of MR-proADM (SEQ ID NO: 2) of greater than 1.04 nmol/L in said specimen correlates with a greater risk of death of said post-myocardial infarction patient.

3. The method of claim 1 further comprising the step of determining the level of NT-proBNP in at least one blood specimen from said post-myocardial infarction patient using an immunoassay, wherein a level of NT-proBNP of greater than 914 pmol/L in said specimen correlates with a greater risk of death of or heart failure in said post-myocardial infarction patient.

4. The method according to claim 1, wherein said adverse event is at least one of myocardial infarction, heart failure and death.

5. The method of claim 1 further comprising the step of determining the level of at least one marker selected from the group consisting of BNP, proBNP, and NT-proBNP, from said post-myocardial infarction patient, wherein a significantly elevated level of said marker, in comparison with post-myocardial infarction patients without adverse events independently correlates with a greater risk of an adverse event in said post-myocardial infarction patient.

6. The method according to claim 5 wherein parallel or simultaneous determinations of the markers are carried out.

7. The method of claim 5 wherein said marker is NT-proBNP.

8. The method according to claim 1 further comprising the step of determining at least one marker selected from the group consisting of inflammatory markers, cardiovascular markers, neurohormonal markers and ischemic markers from said post-myocardial infarction patient.

9. The method according to claim 8, wherein said inflammatory marker is at least one marker selected form the group consisting of C-reactive protein (CRP), procalcitonin (1-116, 3-116), cytokines, interleukins, and adhesion molecules.

10. The method according to claim 9 wherein said cytokine is TNF alpha (tumor necrosis factor-alpha); said interleukin is IL-6, or said adhesion molecule is VCAM or ICAM.

11. The method according to claim 8, wherein said cardiovascular marker is at least one marker selected from the group consisting creatine kinase, myeloperoxidase, myoglobin, natriuretic proteins, cardial troponin, CRP, and circulation-regulating (pro)hormones.

12. The method according to claim 11 wherein said circulation-regulating (pro)hormone is selected from the group consisting of pro-gastrin-releasing peptide (proGRP), pro-endothelin-1, pro-leptin, pro-neuropeptide-Y, pro-somatostatin, pro-neuropeptide-YY, pro-opiomelanocortin and partial sequence thereof in each case.

13. The method according to claim 8, wherein said ischemic marker is at least one marker selected from the group consisting of troponin I and T, and CK-MB.

14. The method according to claim 8, wherein said marker is at least one natriuretic protein.

15. The method according to claim 14, wherein said at least one natriuretic protein is selected from the group consisting of ANP, ANF, proANP, NT-proANP, BNP, proBNP and NT-proBNP.

16. The method according to claim 8 wherein parallel or simultaneous determinations of the markers are carried out.

17. The method according to claim 1, wherein the determination is made in at least one specimen from said post-myocardial infarction patient.

18. The method of claim 17 wherein said specimen is a blood specimen.

* * * * *